United States Patent [19]

Lynch

[11] Patent Number: 4,474,500

[45] Date of Patent: Oct. 2, 1984

[54] REMOVAL OF DENTAL CROWNS WITH WIRE NOOSE

[76] Inventor: Joseph A. Lynch, 51 E. First Ave., Hialeah, Fla. 33010

[21] Appl. No.: 418,570

[22] Filed: Sep. 15, 1982

[51] Int. Cl.$^3$ .............................................. A61C 3/00
[52] U.S. Cl. ..................................... 433/218; 433/161
[58] Field of Search ............... 433/158, 153, 161, 154, 433/218

[56] References Cited

U.S. PATENT DOCUMENTS 3,081,543  3/1963  Schulstad ............................ 433/153
4,230,454  10/1980  Lococo ................................ 433/153

Primary Examiner—Robert Peshock
Attorney, Agent, or Firm—Laurence R. Brown

[57] ABSTRACT

A porcelain crown is non-destructively removed by exerting an upward force on a noose about the neck of the crown from a balanced bar-body resting on the tooth by means of a screw threaded through the bar-body. Balancing is achieved by connecting the noose to the bar-body with a plurality of special straps spaced about the crown circumference and passed over pegs on which cylindrical bushings of various diameters may be placed for changing the effective lengths of the straps. Special light-weight tooling is made feasible for tightening the noose about the crown and clamping it in place so that hands are freed to thereby effect a simpler more efficient crown removal process.

18 Claims, 7 Drawing Figures

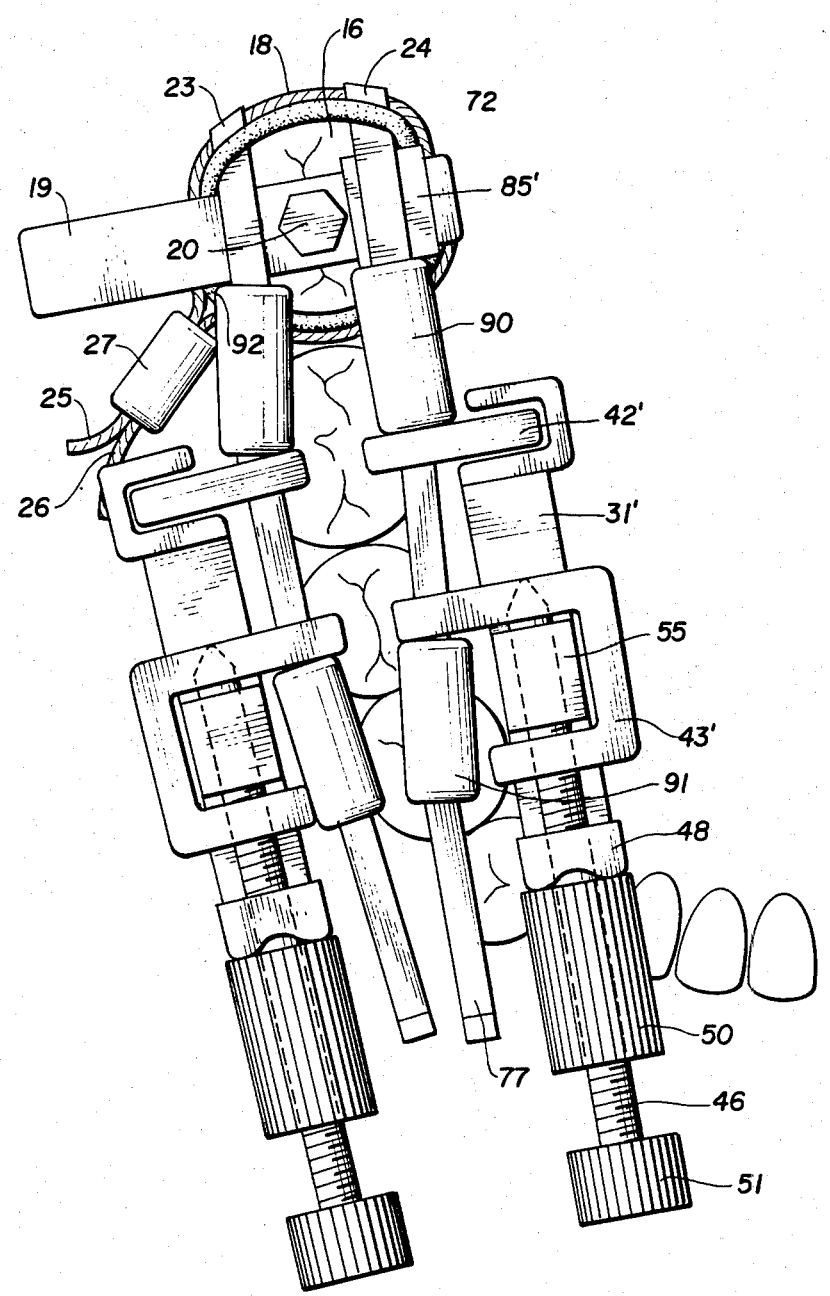

REMOVAL OF DENTAL CROWNS WITH WIRE NOOSE

TECHNICAL FIELD

This invention relates to means and methods for removing dental crowns, and more particularly it relates to the positioning of a wire noose about a crown and exerting an upward pull thereon to dislodge the crown non-destructively.

BACKGROUND ART

This is a continuation-in-part application of the copending application Ser. No. 329,735 filed Dec. 11, 1981 and now U.S. Pat. No. 4,417,876 issued 11/29/83, by the same inventor for "Non-Destructive Dental Cap Removal Means and Methods".

In that application a noose of stranded wire is fitted about the reduced diameter neck portion of the crown close to the gum line. To remove the crown, the noose is pulled upwardly toward the top of the crown away from the gum line by means of metal bands engaging the noose on opposite sides of the crown and engaging an upwardly mobile bar positionable by a screw mechanism extending through the crown top to engage the tooth stub. That prior application is adopted in its entirety herein as a part of the disclosure of this application.

There is no pertinent prior art known relating to the removal of a crown by means of a noose of wire positioned thereabout.

While the removing of crowns by the wire noose method is in general very favorable and removes even delicate porcelain crowns satisfactorily for later reuse, several problems which appear under special circumstances are not resolved heretofore. For example, some crowns require so much force to remove that the wire noose and wire band can stretch, rupture or become displaced.

Also the working space in the mouth is limited particularly in some locations. Thus the several kinds of manual manipulations necessary for removal of a crown need be done in such a way that they do not interfere, that required accessory instruments do not interfere and that the manual functions can preferably be done by a single hand. It is always desirable to reduce the number of steps necessary to achieve the crown removal and the complexity of the steps.

One serious problem is that the instrumentation required for removal of a crown such as the crown removing bar member may tend to tilt or encounter uneven lengths of metal bands, etc. in the crown removal process, thereby requiring repositioning of the bands, noose and/or the bar member.

Another problem in the aforesaid known art is that a stabilizing bar needed to be balanced upon other teeth by means of a cement cushion or the like to form a platform from which the lift is exerted to remove the crown. Thus, a complex, time consuming procedure precedes the lifting of the crown.

It is therefore an object of the present invention to provide means and methods for overcoming these formerly unresolved problems.

DISCLOSURE OF THE INVENTION

Dental crowns are removed by pulling a wire noose tightened about the neck portion of the crown upwardly in a direction away from the gum. A bar member is disposed for crown removal leverage upon at least one tooth and engages the noose on opposite sides of the crown for pulling upwardly by means of interspersed metal bands.

The noose comprising a length of stranded wire with two ends is tightened in situ by clamping together the two loose ends of the wire. A first position near the ends of the wire is clamped to form an anchor point for pushing a second clamp close to the crown to tighten the noose before the two end strands are clamped together to hold the noose in its tightened position.

Instrumentation for removing the crown comprises, the noose with accompanying specially designed fastener devices, in situ noose tightening tool means, the crown removing bar assembly coupled to the noose and specially constructed metal bands connecting the noose to the bar assembly, as disclosed and defined herein. In particular, the novel features of the invention comprise, (1) a small light weight manual screw set tightening tool having two spreader forks for riding over the wire and forcing into position at least one sleeve surrounding the two wire ends which can be crimped in place as the clamping means, (2) a tapered ferrule strain relieving assembly over the two wire ends to permit greater lifting force on the noose, (3) two ply flat welded bands made especially for lifting the noose, (4) the bar assembly with a set of pegs for engaging the bands and (5) means for adjusting tilt of the bar assembly by means of increasing selectively the peg diameters at required locations.

Particularly because of the latter feature, which permits balancing of the bar while under lift load, the bar need not be stabilized against other teeth or be provided with a cement mass cushion, or the like, but significantly simplifies the method by permitting use of a lighter, more local stabilizing bar directly without preconditioning by a stabilizing mass.

BRIEF DESCRIPTION OF THE DRAWINGS

In the drawings:

FIG. 7 is a top view, partly in section to identify elements thereof, looking down at a set of teeth showing the crown remover improvement of this invention with its various elements in place and ready to remove a crown.

THE PREFERRED EMBODIMENTS

Figure 1:
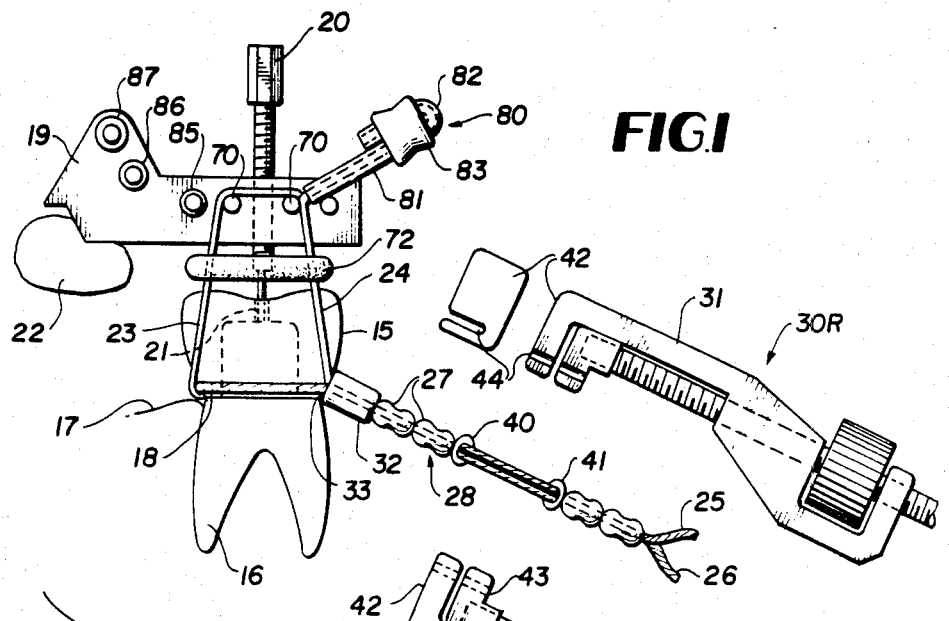
FIG. 1 is a profile view, partly exploded, of the crown removal instrumentation as used for access on either side of the mouth as provided by this invention.

As may be seen from FIG. 1, a porcelain crown 15 caps tooth stub 16 upon which it is cemented. It is to be recognized that if the crown 15 need be removed it is quite delicate, easily fracturable, expensive to reconstruct and is difficult to grasp by conventional tooling with enough force to pull upwardly away from the gum level 17 to remove, especially if the cement bond is strong. In order to non-dectructively remove the crown 15, therefore, as described in my pending application hereinbefore identified, a noose 18 is tightened about the neck of the crown and lifted upwardly away from the gums 17 by means of the bar assembly 19 which presses the screw 20 against tooth stub 16 through a small hole 21 drilled through the crown 15. The bar assembly 19 rests on adjacent teeth (not shown) for support and is held in alignment with screw 20 in hole 21 by means of a cement body 22 or the like. The metal bands 23, 24 (similarly disposed on the opposite side of crown 15) attach noose 18 to the bar 19 to withstand the upward force necessary to remove the crown.

In accordance with the improvements of this present invention, several problems are resolved by novel method steps and corresponding special instrumentation. For example, the working space in the mouth for tightening the noose 18 in situ is limited. Yet to tighten the noose 18, it is required to grasp near the ends 25, 26 of the length of stranded wire forming the noose 18 and force one or more sleeves 27 toward the crown 15 before indenting or crimping them (28) to clamp the pair of wire ends and fix the noose size. Thus, it is desirable to avoid the necessity of holding the wire near ends 25, 26 and forcing sleeves 27 against the crown 18 with one hand while crimping the sleeves 27 with a tool in the other hand. In accordance with this invention therefore a light weight screw set noose tightening instrument 30 that can be set and retain its position while freeing the hands for crimping, etc. is made available. This noose tightening instrument 30 is shown in left hand 30L and right hand 30R versions which can be used for less awkward access to crown positions on right and left sides of the mouth. Other minor variations in structure are also shown where for example the 30R version is a heavier stronger version, by means of framing member 31 which is shown in its lighter weight version 31' for noose tightener 30L.

This noose tightener tool 30 and the alignment of the hollow riders 27, etc. on the double end wires 25, 26 of the noose 18 cooperate in the adjustment of the noose 18 on the neck portion of crown 15 to produce a non-destructive lifting grasp effective in removing the crown. Thus, after the noose wire is looped about the crown neck and the hollow riders 27, etc. threaded thereon, the inner and outer pairs of sleeves 27 are crimped at 28 in position as final clamps after using the tightening tool 30.

The ferrule 32 having a conically tapered inner flanging surface 33 is placed adjacent the crown 15 to serve as a strain relief device for spreading the two wire ends 25, 26 to form the loop. In this fashion the wire noose 18 will be able to withstand far greater upward force from the bands 23, 24 to dislodge crowns more tightly cemented in place.

Two flat washers 40, 41 respectively engage the tightening tool 30 fork member front and rear faces 42, 43 with the fork grooves 44 straddling and riding over the two wire ends 25, 26 therebetween. An end view of face 42 is inserted to show the positioning of the fork grooves in the fork faces 42, etc. As seen by the two views 30L and 30R, one loop tightening tool 30L can be used with forks on top of the wires, and the other 30R with forks below the strands to provide better accessibility as required by choice of the model desired.

The noose tightener tool 30 thus acts as a spreader positioned between washers 40, 41 attempting to spread apart the inner and outer sleeves 27 as the manually set thumb manipulated nut 45 is manipulated on screw 56 to push face 42 outwardly. Thus, if the outer sleeve or sleeves 27 are first crimped and serve as clamps (as shown), then the spreader forces the inner uncrimped sleeve or sleeves 27 toward the crown 15 to tighten noose 18 thereabout and retain the position without further manual intervention until thumb screw 45 is backed off or loosened. Thus, the hands are freed to crimp the inner (tightened) sleeves 27, and thereafter the forks are loosened and tool 30 removed to proceed with the further steps of crown removal.

Figure 5:
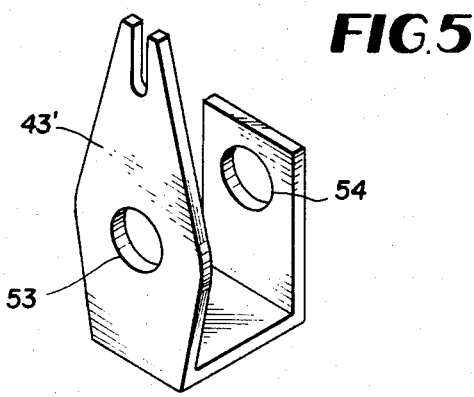
FIG. 5 is a perspective view of a movable fork assembly for the embodiment of FIG. 4.
Figure 4:
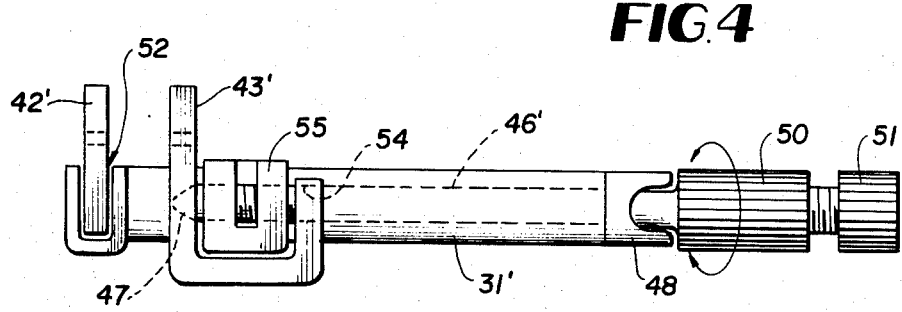
FIG. 4 is a plan view of an alternative noose tightener tool embodiment to that shown in FIG. 1.
Figure 6:
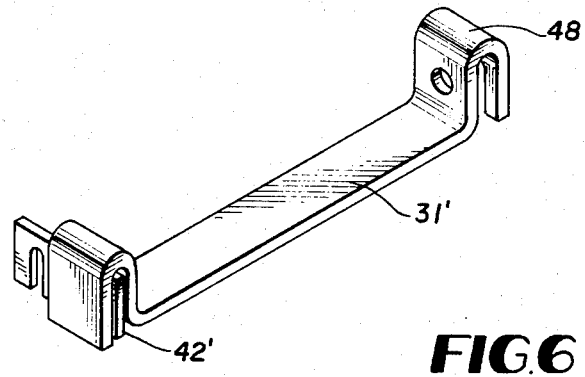
FIG. 6 is a perspective view of a frame member of the FIG. 4 tool.

In the FIG. 4 version, the knurled nut 50 rotates on the screw 46 and is held to the frame 31 by two finger projections of frame 31 and thus moves fork 43 back and forth relative to fork 42 welded in groove 52 or otherwise mounted on frame 31. As the knob 51 of screw 46 is rotated as in screw in motion the rounded end 47 passes thru unthreaded hole 54 of fork assembly into threaded journal 55 and thru 55 into counter sunk or tapered bearing hole 53 of fork assembly 43' thru which it cannot pass. As 47 becomes tight the fork assembly 43' and the screw 46 become tightly jammed with the threaded rider 55 which grips the fork 43' and slides on frame 31. As seen in FIG. 5 the fork assembly 43' has a counter sunk or conically tapered bore 53. As knurled nut 50 is turned on screw 46 this motion carries the fork assembly 43 with journal 55 and the screw 46 back and forth as the gripping flanges of journal 55 slide on the frame 31. Thus the gap is changed to force the washers 40, 41 apart as aforesaid. FIG. 6 shows the frame 31 which supports the screw and slides assembly 43, 55, and 46.

To dislodge the crown 15 from tooth stub 16, the small hole 21 is drilled in the crown to receive the end 60 of screw 20 threaded through bar body 19 to bear on the tooth stub 16. Thus, the bar body 19 may be moved upwardly away from the gum level 17 by means of screw 20. To raise the noose 18 and thus crown 15, the straps 23, 24 are provided at four positions about the circumference of the crown 15 to connect the noose 18 firmly to bar body 19, by means of the pegs 70 extending from opposite sides of the bar body 19, for movement upwardly of the noose 18 and thus crown 15 by force of the screw 20 against tooth stub 16. The rubber O-ring 72 is placed about the plurality of straps 23, 24 to keep them grouped closely about the crown circumference while the straps are crimped and the bar body 19 is positioned, etc.

Figure 3:
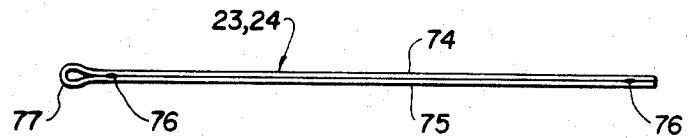
FIG. 3 is a side view of the special bands used in accordance with this invention showing their construction.

The straps are critical and thus comprise two layers 74, 75 of flat metal strip shown in side view in FIG. 3. They are welded together at 76, 77 near the ends to form a double layer unitary strap of greater strength, having a loop 77 therein that can be threaded over the wire of noose 18 before tightening in place. These straps further have significant interaction utility in the instrumentation and method of crown removal afforded by this invention, as will be discussed hereinafter.

As best seen in FIG. 1, two straps 23, 24 are fastened together at ends 80 after passing over the respective pegs 70 in the bar body 19. Thus, they are tautened and a first sleeve 81 is crimped thereover as a clamp. Thereafter the ends are folded over 82 and a second outer sleeve 83 crimped in place. Thus the joint withstands the necessary lifting force to remove the crown 15. The straps may then be tightened by means of screw 20.

Figure 2:
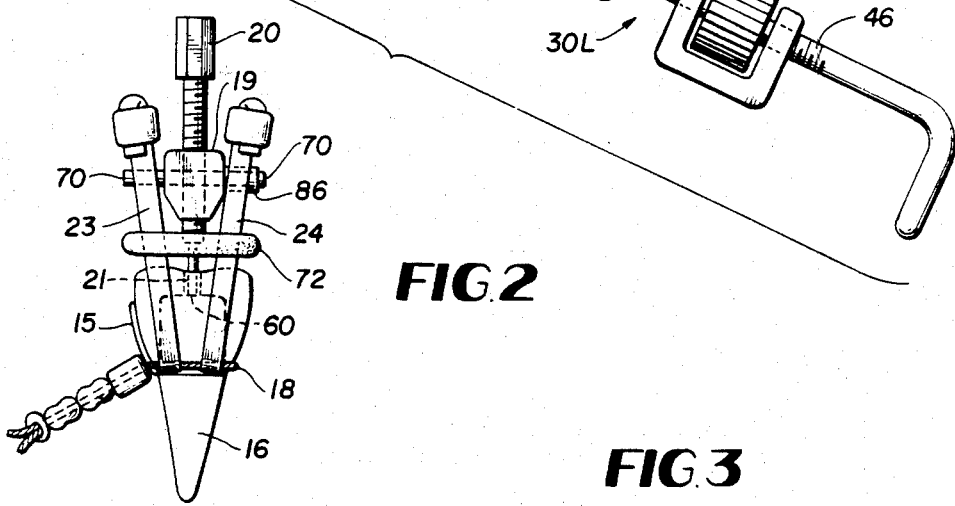
FIG. 2 is an end view of a portion of the assembly in FIG. 1.

Note that some of the pegs of bar body 19 have cylindrical bushings thereover of several diameters, 85, 86, 87, etc. These are critical to the present invention instrumentation and structure and permit a mode of operation not heretofore contemplated. Thus, formerly the bar body 19 was balanced or stabilized by a cement cushion or body 22 on other teeth than that 16 having the crown 15 removed therefrom. This is because of some difficulty in exactly aligning screw 20 without some tilt or unbalance passed into bar body 19, particularly when the upward force is exerted, which in the case of a difficult to remove crown can become great. With the bushings 86, etc., however, the forces can be readily balanced so that the bar body 19 need not be rested upon other teeth or have a cushion body 22 interspersed for stabilization. That is as seen best from FIG. 2, the bar body 19 rests only upon tooth stub 16 by means of screw tip 60 for the crown removal. Thus, the body may be simplified in shape and reduced in weight, although a shape as shown in FIG. 1 might be desirable for use in special situations such as with crooked teeth, or bridges, etc.

The cylindrical bushings 85, etc. can also be flattened so that adjustment may be made by rotation thereof. An alternate manner of balancing the bar body 19 as needed when the force is applied to break loose the crown is shown in FIG. 7. Therein an equivalent metal balancing pad 85' is placed under band 24 and on top of bar 19 when the band 24 stretches enough to unbalance the removal force on the crown imposed by screw 20. This shimming procedure is an important feature of the invention since porcelain crowns are very delicate and are easily broken by any unbalanced forces exerted on their thin skirts. As described in the parent application, the skirts may be strengthened by the addition of a plate 92 receiving the noose.

In FIG. 7 like reference characters are used for comparison to show the relationships of the various elements in the mouth. Note that everything is accessible from the front of the mouth, such as for example the band tightening tools which force apart the two sleeves 90, 91 for tightening the bands 23, 24 in the manner hereinbefore described. The rubber O-ring 72 position and stranded wire noose 18 are exaggerated in position somewhat to show their arrangement in the assembly.

This embodiment simply passes the bands 23, 24 over the bar 19 to straddle it thereby simplifying the shape of the stabilizing or balancing bar member 19.

Note also metal plate 92 which is inserted between the noose 18 and the porcelain crown as described in the parent application for the purpose of protecting the very fragile buccal or labial margin of a porcelain crown near the gum line.

Thus for the first time a porcelain crown can be removed non-destructively simply by connecting a wire noose about the neck of the crown by means of straps to a balanced bar body resting upon the crowned tooth and exerting an upward force, preferably by means of a screw through the bar body to remove the crown.

Having therefore improved the state of the art those novel features believed descriptive of the spirit and nature of the invention are defined with particularity in the claims.

I claim:

1. The method of removing dental crowns on tooth stubs by pulling in a direction away from the gum a noose circumferentially surrounding a neck portion of the crown near the gum by means of an upwardly mobile crown removing bar member disposed for crown removal leverage upon at least one tooth and having said bar member connected for moving the noose upwardly by metal bands disposed on opposite sides of the crown connected between the noose and the bar member, wherein the noose is formed by a length of wire fitted about the crown and tightened in place therearound by means of two sleeves surrounding the two loose ends of the wire, characterized by the steps of, retaining the noose in place about said crown by fixing one of said sleeves in place to clamp the two loose ends of the wire together, moving the other said sleeve on the wire ends toward the tooth by pressure against the said clamped sleeve to a position close to said crown to tighten the noose for moving the other sleeve over the two loose ends of the wire until the noose is tightened, retaining the other sleeve in place with the noose tightly retained about the crown, drilling a hole through the crown to the tooth stub, locating a bar member having a screw extending therethrough to extend through the hole and bear on the tooth stub, connecting said bar to said noose with bands disposed on opposite sides of the tooth, and moving said bar member upwardly by means of said screw to pull the noose and crown upwardly off the tooth stub.

2. The method of claim 1 including the further step of relieving strain on said noose where the two ends of the wire are adjacent the surface of the crown by inserting between said other sleeve and the crown a ferrule having conically flared lips adjacent the crown to form a shaped transition zone between the two adjacent ends passing through the other sleeve and the noose about the crown.

3. The method of claim 1 including the further steps of, folding flat metal strips to form double layer bands having a loop at one end, threading four folded bands on the noose portion of the wire for positioning two bands on each opposite side of the crown before tightening the noose about the crown, and fixing the bands tightly in place on the bar member after the noose is tightened.

4. The method of claim 3 including the further step of grouping the bands close to the crown with a rubberlike O-ring placed about the four bands near the top of the crown.

5. The method of claim 3 including the step of welding of the bands near each end after folding.

6. The method of claim 3 including the further step of positioning said bar member for receiving and holding said bands.

7. The method of claim 6 including the further steps of providing extension pegs from the bar member to mate with and hold the bands, passing the ends of two bands located on one side of the crown about two of said extension pegs to thereby meet at a single clamping site, and clamping the two bands together at said site to retain the two bands on the bar.

8. The method of claim 6 including the further steps of passing the bands over the bar to straddle it, and therafter clamping the two ends of the band together at the site.

9. The method of claim 6 including the further step of adjusting tilt of said bar by means of inserting a shimming member to thereby reposition one of the two said bands on one side of the crown.

10. The method of claim 8 including the step of adjusting the position of the band by means of a pad positioned between the band and the bar.

11. The method of claim 6 including the additional steps of supporting the bar member against only the tooth from which the crown is to be removed, balancing the bar by selecting the engagement positions of said metal bands on said bar to remove the crown without substantial tilting of the balanced bar.

12. The method of removing crowns defined in claim 1 including the steps of supporting said bar member against only the one tooth from which the crown is to be removed, and balancing the bar to withstand said upward force without substantial tilt.

13. The method of removing crowns as defined in claim 1 comprising the step of placing a metal plate between the noose and the crown.

14. Instrumentation made specially to carry out any one of the method steps defined in claims 1 to 11.

15. The method defined in claim 1 including the step of clamping the other sleeve to the two ends of the wire in a position to hold the noose tightly about the crown.

16. The method defined in claim 1 wherein the step of moving the other sleeve comprises engaging the two sleeves with two members on an instrument that are movable apart by a screw threaded member.

17. The simplified method of non-destructively removing dental crowns comprising the steps of resting a body by means of a screw therethrough extending through the crown to a tooth stub upon which a crown resides, placing a wire noose about the crown at a reduced circumference neck portion thereof, coupling the noose to the body at a plurality of positions about the circumference of the crown by means of connecting force transmitting straps to the noose and body for lifting the crown from said tooth, balancing the body for support solely upon said tooth by selecting the position of the straps on the body, and exerting an upward force on said balanced body by means of said screw thereby to remove the crown by lifting said noose upwardly.

18. The method of removing crowns as defined in claim 17 comprising the step of placing a metal plate between the noose and the crown for the purpose of protecting the very fragile buccal or labial margin of a porcelain crown near the gum line.

* * * * *